(12) United States Patent
Russo

(10) Patent No.: US 10,363,039 B2
(45) Date of Patent: Jul. 30, 2019

(54) SURGICAL FASTENER APPLIERS

(71) Applicant: Covidien LP, Mansfield, MA (US)

(72) Inventor: Mark Russo, Plantsville, CT (US)

(73) Assignee: Covidien LP, Mansfield, MA (US)

( * ) Notice: Subject to any disclaimer, the term of this patent is extended or adjusted under 35 U.S.C. 154(b) by 364 days.

(21) Appl. No.: 15/340,261

(22) Filed: Nov. 1, 2016

(65) Prior Publication Data

US 2017/0143342 A1    May 25, 2017

Related U.S. Application Data

(60) Provisional application No. 62/258,102, filed on Nov. 20, 2015.

(51) Int. Cl.

| | | |
|---|---|---|
| *A61B 17/10* | (2006.01) | |
| *A61B 17/08* | (2006.01) | |
| *A61F 2/00* | (2006.01) | |
| *A61B 17/068* | (2006.01) | |
| *A61B 17/064* | (2006.01) | |
| *A61B 17/29* | (2006.01) | |
| *A61B 90/00* | (2016.01) | |

(52) U.S. Cl.
CPC .......... *A61B 17/105* (2013.01); *A61B 17/068* (2013.01); *A61B 17/08* (2013.01); *A61F 2/0063* (2013.01); *A61B 2017/0648* (2013.01); *A61B 2017/2903* (2013.01); *A61B 2090/0803* (2016.02); *A61B 2090/0807* (2016.02); *A61B 2090/0814* (2016.02)

(58) Field of Classification Search
CPC ..... A61B 17/08; A61B 17/105; A61B 17/068; A61B 2017/0648; A61B 2017/2903; A61B 2090/0803; A61B 2090/0814; A61B 2090/0807; A61F 2/0063; B25C 1/184; B25C 1/186; B25C 5/1627; B25C 5/1689
See application file for complete search history.

(56) References Cited

U.S. PATENT DOCUMENTS

| | | |
|---|---|---|
| 5,582,616 A | 12/1996 | Bolduc et al. |
| 5,810,882 A | 9/1998 | Bolduc et al. |
| 5,830,221 A | 11/1998 | Stein et al. |

(Continued)

FOREIGN PATENT DOCUMENTS

| | | |
|---|---|---|
| EP | 0 769 275 A1 | 4/1997 |
| EP | 2361559 A1 | 8/2011 |

(Continued)

OTHER PUBLICATIONS

Extended European Search Report corresponding to counterpart Int'l, Appln. No. EP 16 19 9743.2 dated Apr. 12, 2017.

*Primary Examiner* — Alexander M Valvis
*Assistant Examiner* — Thomas M Wittenschlaeger

(57) ABSTRACT

An end effector is provided and includes an outer tube, a coil member, a plurality of fasteners, and an engagement member. The outer tube defines a viewing window and a lockout window. The coil member is disposed within the outer tube. The plurality of fasteners are disposed in the coil member. The engagement member is disposed proximal to the plurality of fasteners and is visible through the viewing window of the outer tube. The engagement member is configured to translate proximal to the plurality of fasteners to provide a count of the plurality of fasteners remaining in the end effector.

19 Claims, 6 Drawing Sheets

(56) References Cited

U.S. PATENT DOCUMENTS

| | | | |
|---|---|---|---|
| 5,868,761 A * | 2/1999 | Nicholas | A61B 17/1285 606/139 |
| 8,474,679 B2 * | 7/2013 | Felix | A61B 17/064 227/175.1 |
| 8,713,835 B1 * | 5/2014 | Calvert | F41A 9/71 42/49.01 |
| 9,867,620 B2 * | 1/2018 | Fischvogt | A61B 17/12013 |
| 2002/0058967 A1 * | 5/2002 | Jervis | A61B 17/064 606/213 |
| 2002/0068947 A1 | 6/2002 | Kuhns et al. | |
| 2003/0009441 A1 | 1/2003 | Holsten et al. | |
| 2003/0111239 A1 * | 6/2003 | Smolinski | B25C 1/005 173/8 |
| 2003/0135226 A1 | 7/2003 | Bolduc et al. | |
| 2004/0133214 A1 | 7/2004 | Kayan | |
| 2004/0153101 A1 | 8/2004 | Bolduc et al. | |
| 2005/0187613 A1 * | 8/2005 | Bolduc | A61B 17/064 623/1.23 |
| 2005/0240222 A1 | 10/2005 | Shipp | |
| 2005/0267478 A1 | 12/2005 | Corradi et al. | |
| 2006/0079913 A1 * | 4/2006 | Whitfield | A61B 17/10 606/142 |
| 2006/0108391 A1 * | 5/2006 | Leasure | B25C 1/047 227/120 |
| 2006/0122636 A1 | 6/2006 | Bailly et al. | |
| 2006/0129154 A1 | 6/2006 | Shipp | |
| 2007/0038220 A1 | 2/2007 | Shipp | |
| 2007/0250064 A1 | 10/2007 | Darois et al. | |
| 2008/0045978 A1 | 2/2008 | Kuhns et al. | |
| 2008/0086154 A1 | 4/2008 | Taylor et al. | |
| 2008/0097523 A1 | 4/2008 | Bolduc et al. | |
| 2008/0277445 A1 * | 11/2008 | Zergiebel | A61B 17/064 227/132 |
| 2008/0281353 A1 * | 11/2008 | Aranyi | A61B 17/064 606/219 |
| 2010/0270354 A1 | 10/2010 | Rimer et al. | |
| 2010/0312257 A1 | 12/2010 | Aranyi | |
| 2011/0022065 A1 | 1/2011 | Shipp | |
| 2011/0071578 A1 * | 3/2011 | Colesanti | A61B 17/064 606/305 |
| 2012/0022557 A1 | 1/2012 | Cabiri et al. | |
| 2012/0074194 A1 * | 3/2012 | Miller | B25C 1/008 227/8 |
| 2012/0241490 A1 | 9/2012 | Busch et al. | |
| 2014/0243855 A1 * | 8/2014 | Sholev | A61B 17/064 606/139 |
| 2014/0257339 A1 * | 9/2014 | Levy | A61B 17/068 606/139 |
| 2014/0276967 A1 * | 9/2014 | Fischvogt | A61B 17/12013 606/139 |
| 2014/0276969 A1 * | 9/2014 | Wenchell | A61B 17/10 606/139 |
| 2014/0276972 A1 * | 9/2014 | Abuzaina | A61B 17/064 606/143 |

FOREIGN PATENT DOCUMENTS

| | | |
|---|---|---|
| WO | 2013/004947 A1 | 1/2013 |
| WO | 2013/046115 A1 | 4/2013 |

* cited by examiner

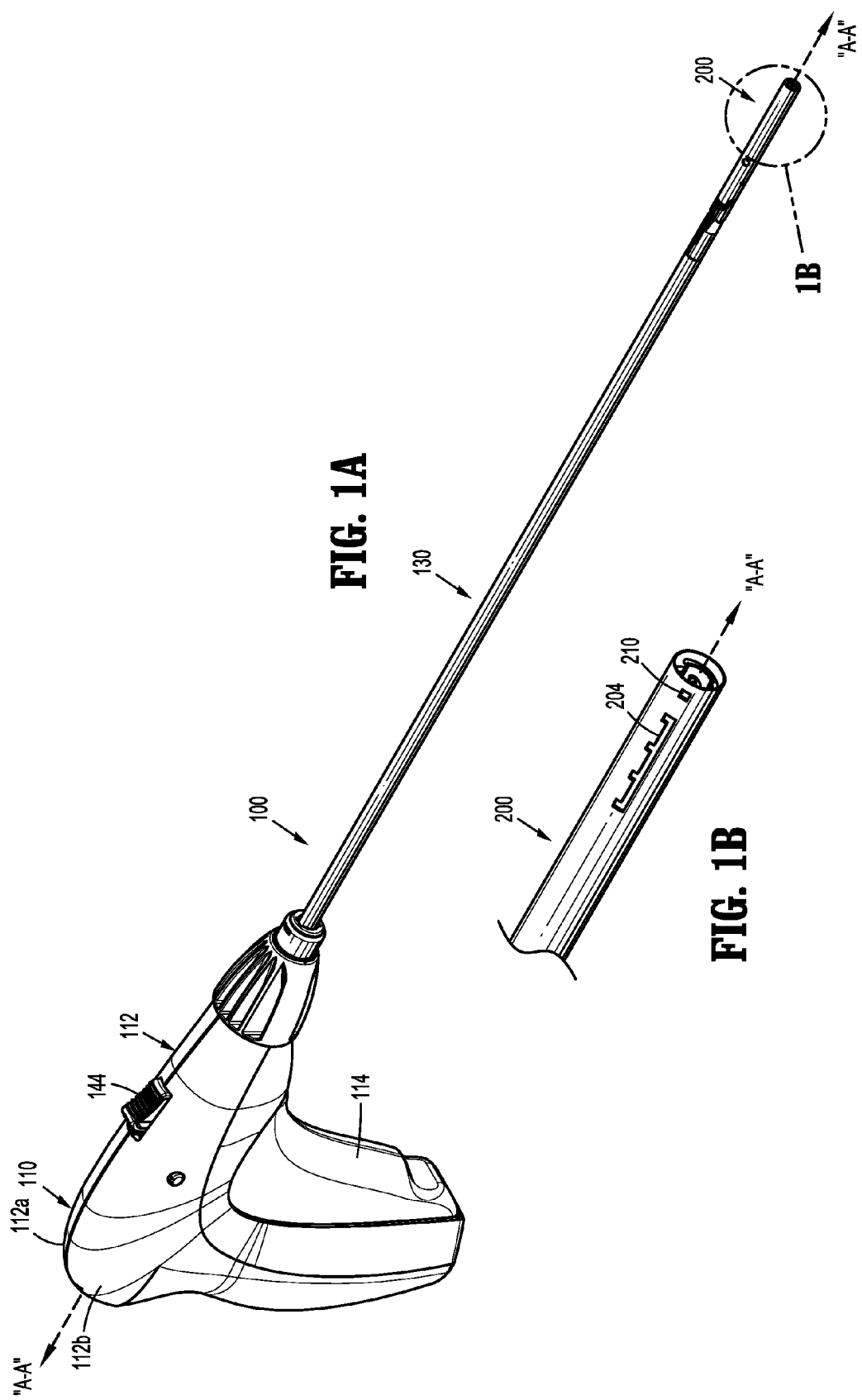

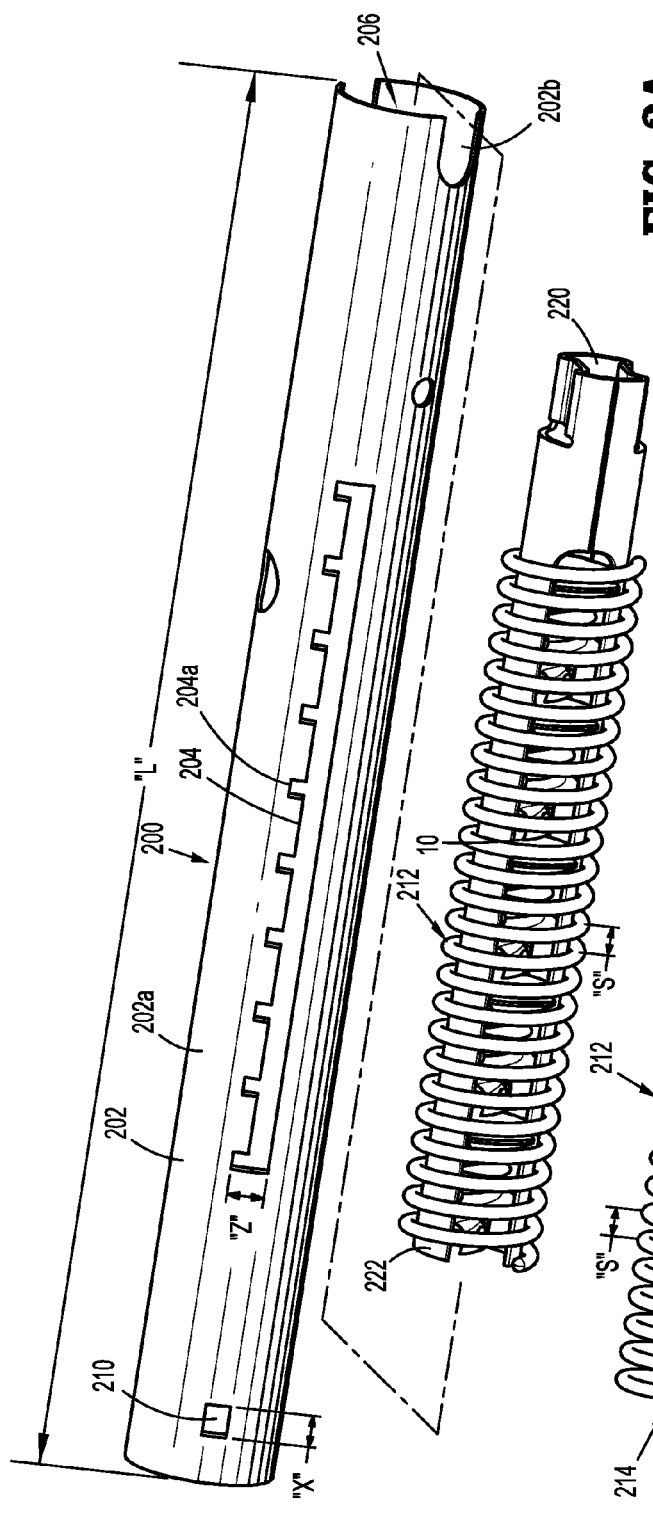
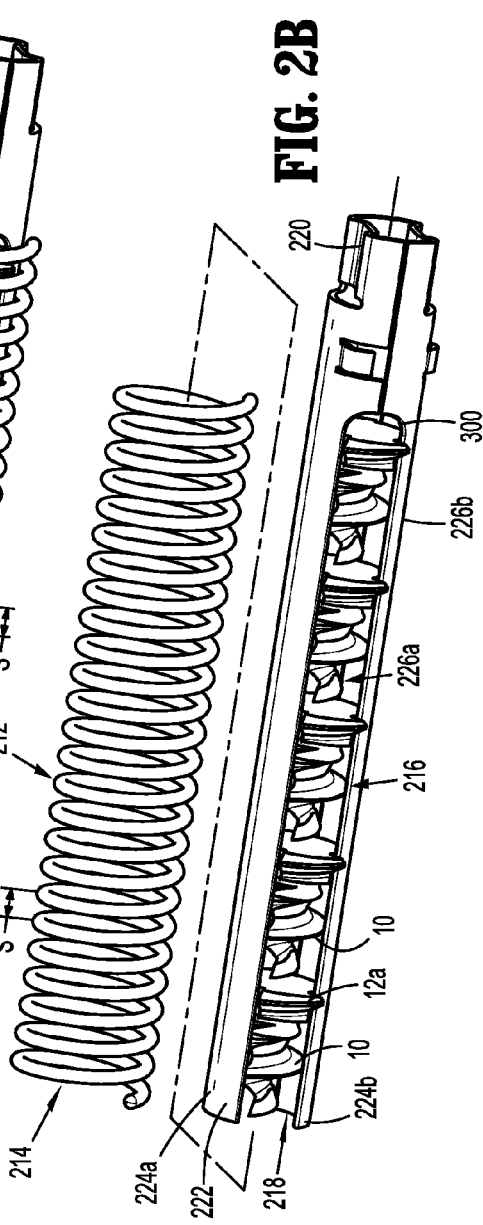
FIG. 2A
FIG. 2B

SURGICAL FASTENER APPLIERS

CROSS-REFERENCE TO RELATED APPLICATIONS

This application claims the benefit of and priority to U.S. Provisional Patent Application No. 62/258,102 filed Nov. 20, 2015, the entire disclosure of which is incorporated by reference herein.

BACKGROUND OF THE INVENTION

1. Technical Field

The present disclosure relates to surgical fastener appliers, and more particularly, to surgical tack appliers having surgical fasteners including engagement members and associated methods of applying.

2. Description of Related Art

In hernias, such as direct or indirect inguinal hernias, a part of the intestine protrudes through a defect in the support abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

In contrast, minimally invasive, e.g., endoscopic or laparoscopic, surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body.

Currently, minimally invasive surgical techniques for hernia repair utilize surgical fasteners, e.g., surgical tacks, staples, and clips, to secure the mesh to the tissue to provide reinforcement to the repair and structure for encouraging tissue ingrowth. Surgical fasteners may be deployed with a surgical fastener applier through a mesh and into tissue below.

Challenges may be presented in affixing a mesh over a hernial defect with surgical fasteners, e.g., in instances involving irregular or uneven surface geometries, or in situations when internal body structures are subject to movement and shifting. However, it is desirable to minimize the number and size of surgical fasteners deployed through a mesh to minimize trauma to the tissue below. Accordingly, it would be desirable to provide a surgical fastener that is configured with optimized mesh retention properties, while minimizing the portion or size of the surgical fastener inserted into tissue.

Further, it would also be desirable to provide a means of counting the surgical fasteners remaining in the surgical fastener applier as surgeons may put down the surgical fastener applier when surgical fasteners remain, pick up the surgical fastener applier for later use during the procedure, and forget the number of surgical fasteners that still remain in the surgical fastener applier.

SUMMARY OF THE INVENTION

According to an aspect of the present disclosure, an end effector is provided and includes an outer tube, a coil member, a plurality of fasteners, and an engagement member. The outer tube defines a viewing window and a lockout window. The outer tube also defines a first passageway therethrough. The coil member is disposed within the first passageway of the outer tube, the coil member defining a second passageway therethrough. The plurality of fasteners are disposed in the second passageway of the coil member, the plurality of fasteners are configured to translate along the second passageway. The engagement member is disposed proximal to the plurality of fasteners and is visible through the viewing window of the outer tube, the engagement member is configured to translate along the second passageway proximal to the plurality of fasteners to provide a count relative to the viewing window of the plurality of fasteners remaining in the end effector. The engagement member includes a body portion and a biasing portion extending from the body portion. The biasing portion includes a biasing arm, the biasing arm biased resiliently outward such that engagement of a free end of the biasing portion of the engagement member with the lockout window restricts further translation of the engagement member.

The outer tube may include indicia disposed along the viewing window to indicate the count of the plurality of fasteners remaining in the end effector.

The outer tube may include the biasing arm of the engagement member to include a first biasing arm and a second biasing arm and a pair of lockout windows configured to engage with the first and second biasing arms of the engagement member.

The end effector may further include an inner tube rotatably supported in the second passageway of the coil member, the inner tube defining a third passageway. The inner tube may include a first tine and a second tine, wherein the first and second tines are radially opposed and define a first channel and a second channel therebetween.

The plurality of fasteners may be disposed in the third passageway of the inner tube. The plurality of fasteners may each include a pair of opposed threaded portions. The threaded portions of the plurality of fasteners may be configured to extend radially beyond the first channel and the second channel of the inner tube respectively.

The threaded portions of the plurality of fasteners may be configured to engage a plurality of successive winds of coil of the coil member.

The engagement member may include a body and a pair of a threaded portions protruding radially from the body thereof.

The first and second biasing arms may be approximated radially-inward toward the body of the engagement member in a first configuration of the engagement member.

The first and second biasing arms may be disposed radially-outward with respect to the body of the engagement member in a second configuration of the engagement member, when the free end of the biasing arm is in registration with the lockout window.

A width of a head portion of each of the first and second biasing arms may be greater than a width of the viewing window such that the head portions of the first and second biasing arms do not engage the viewing window during actuation of the end effector.

A thickness of a head portion of each of the first and second biasing arms may be smaller than a width of each lockout window such that the head portions of the first and second biasing arms engage respective lockout windows, when the head portions of the first and second biasing arms are in registration with the respective lockout windows.

In use, when the head portions of the first and second biasing arms of the engagement member engage the respective lockout windows, and when the threaded portions of the body of the engagement member engage the inner tube, the inner tube may be unable to rotate relative to the outer tube.

According to another aspect of the present disclosure, an end effector is provided and includes an outer tube, a coil member, an inner tube, a plurality of fasteners, and an engagement member. The outer tube defines a viewing window and a lockout window. The outer tube also defines a first passageway therethrough. The coil member is disposed within the first passageway of the outer tube, the coil member defining a second passageway therethrough. The inner tube is rotatably supported in the second passageway of the coil member and defines a third passageway. The inner tube includes a first tine and a second tine, wherein the first and second tines are radially opposed and define a first channel and a second channel therebetween. The plurality of fasteners are disposed in the third passageway of the inner tube, the plurality of fasteners are configured to translate along the third passageway.

The engagement member is disposed proximal to the plurality of fasteners and is visible through the viewing window of the outer tube, the engagement member is configured to translate along the third passageway proximal to the plurality of fasteners to provide a count of the plurality of fasteners remaining in the end effector. The engagement member includes a body portion and a biasing portion extending from the body portion. The biasing portion includes a first biasing arm and a second biasing arm, the first and second biasing arms biased resiliently outward such that engagement of a free end of the biasing portion of the engagement member with the lockout window restricts further translation of the engagement member.

The outer tube may include a pair of opposing lockout windows configured to engage with the first and second biasing arms of the engagement member.

The opposing lockout windows may be located on the outer tube such that when a last fastener of the plurality of fasteners is fired, the first and second biasing arms of the engagement member are in registration with the respective lockout windows.

BRIEF DESCRIPTION OF THE DRAWINGS

Embodiments of the present disclosure will be appreciated by reference to the drawings, wherein:

FIG. 1A is a side, perspective view of a tack applier according to the present disclosure;

FIG. 1B is an enlarged view of the indicated area of detail of FIG. 1A;

FIG. 2A is a side, perspective view of an end effector according to the present disclosure with an outer tube thereof separated therefrom;

FIG. 2B is a side, perspective view of an inner tube and a coil member of the end effector of FIG. 2A;

DETAILED DESCRIPTION

Figure 3:
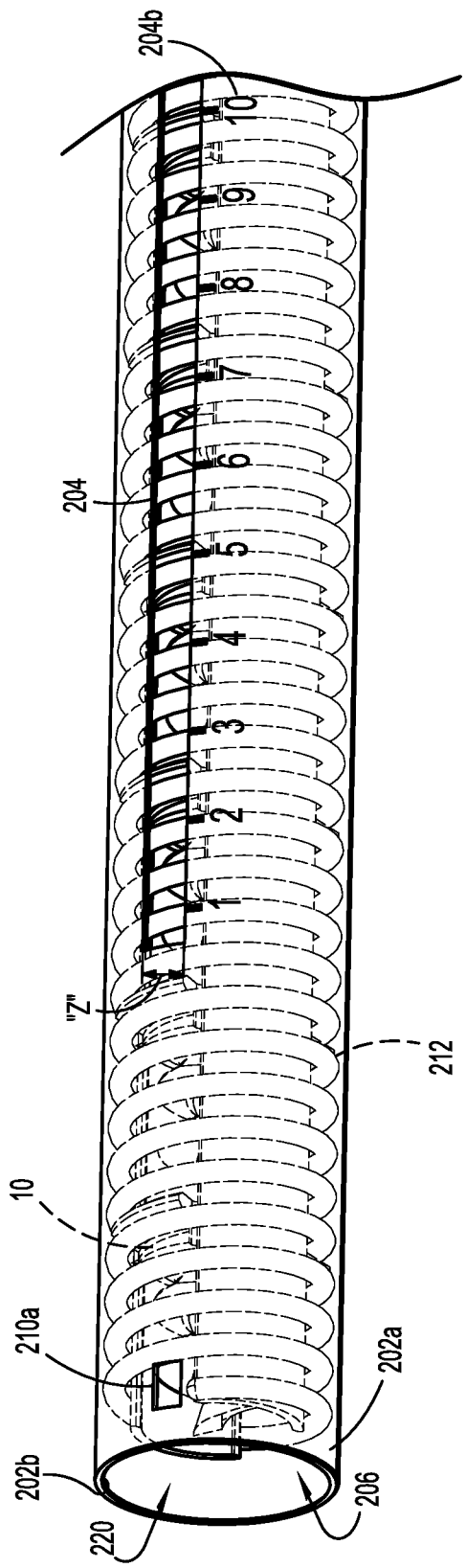
FIG. 3, is a side, phantom perspective view of another embodiment of an end effector according to the present disclosure.

With reference now to the drawings wherein like numerals represent like elements throughout the several views, the presently-disclosed surgical fastener will be described. As used herein, the term "operator" may refer to any user, e.g., a nurse, doctor, or clinician, of the presently-disclosed surgical fastener. Further, the term "distal" refers to that portion of the surgical fastener, or component thereof, further from the operator while the term "proximal" refers to that portion of the surgical fastener, or component thereof, closer to the operator.

Referring initially to FIG. 1A, an endoscopic surgical device, in the form of an endoscopic surgical tack applier or tacker, is shown generally as 100. Tack applier 100 includes a handle assembly 110, and an endoscopic assembly 130 extending from handle assembly 110

Continuing with FIG. 1A, handle assembly 110 includes a handle housing 112 formed from a first half-section 112a and a second half section 112b joined to one another. First half-section 112a and second half section 112b of handle housing 112 may be joined to one another using know methods by those of skill in the art, including and not limited to welding, fasteners (i.e., screws) and the like. Handle assembly 110 also includes a trigger 114 pivotably connected to handle housing 112, at a location remote from endoscopic assembly 130.

Figure 8:
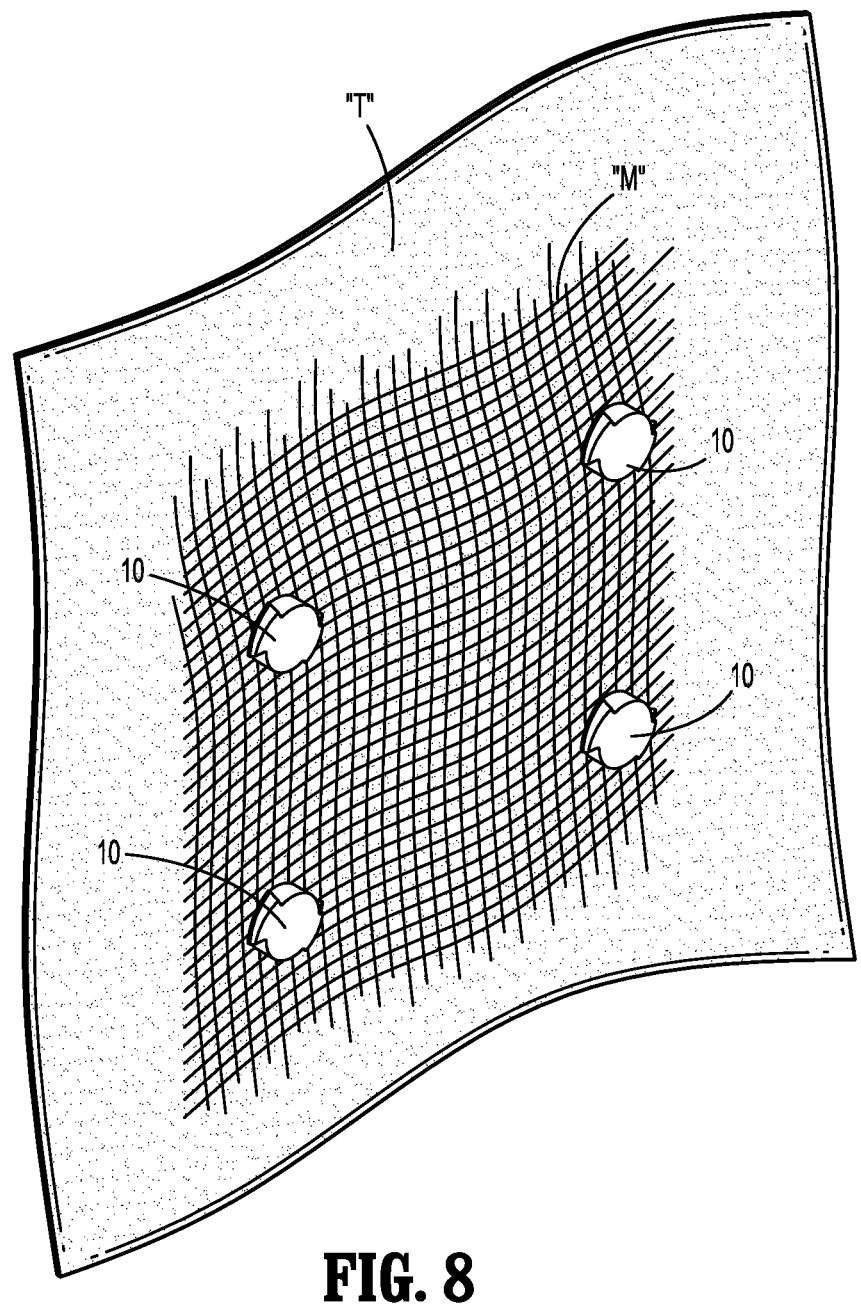
FIG. 8 is a top plan view of the fastener deployed into a mesh and tissue according to the present disclosure.

Handle assembly 110 includes a load/release slider 144 slidably supported on handle housing 112 and being configured to effectuate a loading/retention and a release/removal of an end effector 200, in the form of a single use loading unit (SULU) or disposable loading unit (DLU), as will be discussed in greater detail below. As shown in FIG. 1A, end effector 200 is releasably connected to endoscopic assembly 130 and is configured to store and selectively release or fire a plurality of fasteners 10 (FIG. 4) therefrom and into mesh "M" overlying tissue "T" (FIG. 8).

Turning now to FIGS. 1B, 2A, 2B, and 3, end effector 200 as briefly described above, is shown. End effector 200 includes an outer tube 202 having an outer surface 202a and an inner surface 202b. Outer surface 202a defines a viewing window 204, extending longitudinally along a length "L" of end effector 200. Inner surface 202b of outer tube 202 defines a first passageway 206, extending longitudinally along length "L" of end effector 200. Viewing window 204 is configured such that an engagement member 300, as will be discussed in greater detail below, can be located within end effector 200 by a user. It is contemplated that a user can use the location of the engagement member 300 with respect to the viewing window 204 to keep count of the number of fasteners 10 left in end effector 200. To this end, viewing window 204 includes indicia, such as, for example, a plurality of graduated cutouts 204a corresponding with the number of fasteners 10 loaded in end effector 200. The position of engagement member 300 with respect to the plurality of graduated cutouts 204a will inform a user of the number of fasteners 10 left in end effector 200.

Figure 7A:
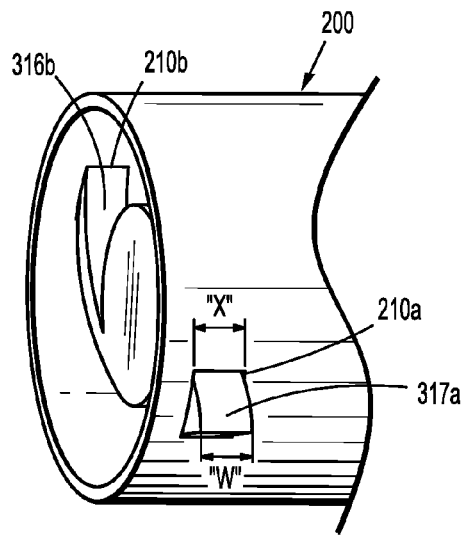
FIG. 7A is a side, perspective view of a distal portion of the end effector, shown in a locked out configuration.
Figure 7B:
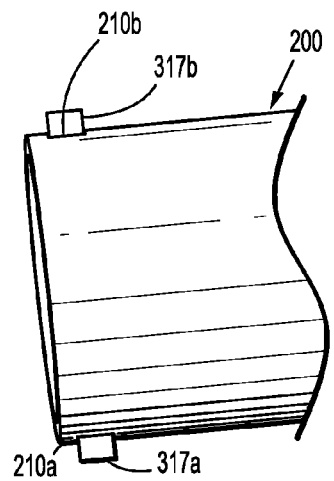
FIG. 7B is a top, view of the distal portion of the end effector, shown in the locked out configuration.

In one embodiment, as shown in FIG. 3, the indicia may also be a plurality of numbers 204b to achieve the same purpose. Outer surface 202a also defines a pair of opposing lockout windows 210a, 210b extending through outer tube 202 (FIG. 7B). As will be discussed in greater detail below, engagement member 300 is configured to engage the opposing lockout windows 210a, 210b such that, upon engagement, further actuation of end effector 200 is mechanically prevented.

As shown in FIGS. 2A and 2B, end effector 200 includes a coil member 212 disposed therein. Coil member 212 is a substantially resilient member that is biased to return to a resting position under a bending load. Coil member 212 is fixedly disposed within outer tube 202 and may be attached to the inner surface 202b of outer tube 202 in any suitable manner, e.g., adhesion brazing or welding. Coil member 212 is disposed in a helically wound configuration such that successive winds of coil member 212 define longitudinal spaces "S" between adjacent winds of the coil member 212. Coil member 212 defines a second passageway 214.

In one embodiment, end effector 200 may also include an inner tube 216 rotatably disposed within coil 212. Inner tube 216 defines a third passageway 218 therethrough, and includes a proximal end portion 220 and a splined distal end portion 222. Proximal end portion 220 of inner tube 216 is configured and dimensioned to releasably connect to endoscopic assembly 130. Splined distal end portion 222 of inner tube 216 is slotted, defining a pair of tines 224a and 224b and a pair of channels 226a and 226b.

The plurality of fasteners 10 may be loaded into end effector 200 in any suitable manner. Though not shown in the figures, in one embodiment, the plurality of fasteners 10 may be loaded directly into the second passageway 214 of coil member 212. Coil member 212 has a configuration such that opposing threaded portions 12a, 12b extending from a head 12 of fastener 10 may be disposed within the longitudinal spaces "S" between adjacent winds of coil member 212.

In another embodiment, as shown in FIG. 2B, splined distal end portion 222 of inner tube 216 is capable of accepting the plurality of fasteners 10 within third passage 218. In particular, the plurality of fasteners 10 may be loaded into end effector 200 such that the pair of opposing threaded sections 12a, 12b of fastener 10 extends through respective channels 226a and 226b of inner tube 216 and are slidably disposed within the longitudinal spaces "S" between adjacent winds of coil member 212. Each fastener 10 is loaded into end effector 200 such that adjacent fasteners 10 are not in contact with one another so as to not damage distal tip 14 of each fastener 10.

Engagement member 300 is loaded into end effector 200 and is disposed proximal to the plurality of fasteners 10. In one embodiment not shown in the figures, engagement member 300 may be loaded directly into the second passageway 214 of coil member 212. In this embodiment, opposing threaded portions 312a, 312b of engagement member 300 may be disposed within the longitudinal spaces "S" between adjacent winds of coil member 212. In another embodiment as shown in FIG. 2B, engagement member 300 may be loaded into the third passageway 218 of inner tube 216 proximal to the plurality of fasteners 10.

Figure 4:
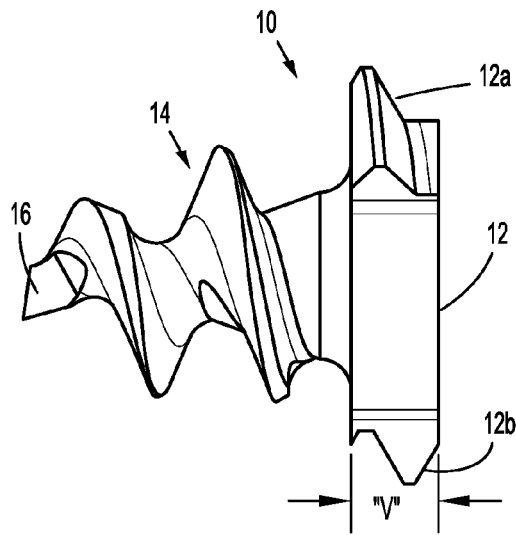
FIG. 4 is a side, plan view of a fastener according to the present disclosure.
Figure 5A:
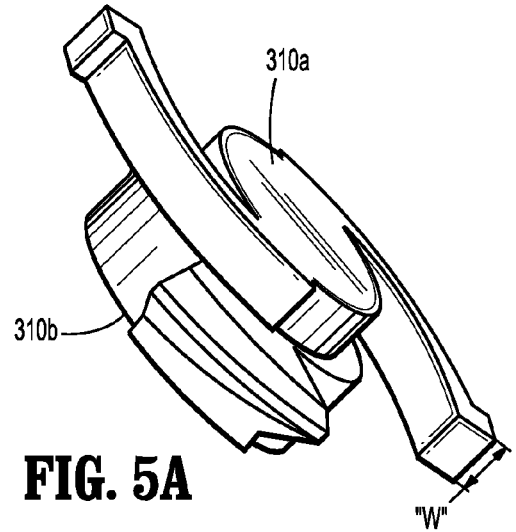
FIGS. 5A-5B are perspective views of an engagement member shown in a second configuration, according to the present disclosure.
Figure 5B:
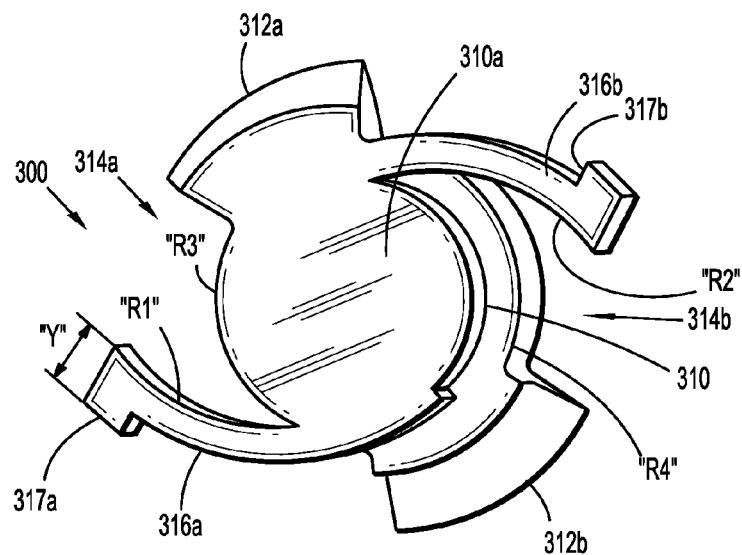
Figure 6:
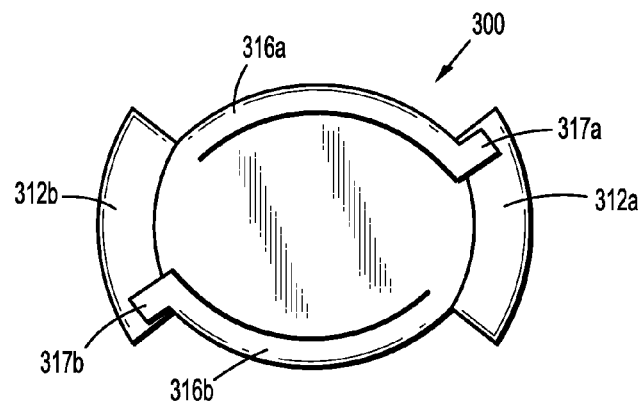
FIG. 6 is a rear, plan view of the engagement member of FIGS. 5A-5B shown in in a first configuration, according to the present disclosure.

Turning now to FIGS. 4-6, engagement member or lockout member 300 according to an embodiment of the present disclosure is shown. Engagement member 300 includes a body 310 having a substantially flat, disc-like profile that has a proximal surface 310a and a distal surface 310b. As briefly noted above, engagement member 300 includes two opposing threaded portions 312a and 312b. Opposing threaded portions 312a and 312b protrude radially outwardly from body 310 and are configured for engagement with channels 226a, 226b of inner tube 216 of end effector 200. A pair of radial gaps 314a, 314b is defined between the opposing threaded portions 312a, 312b of body 310 of engagement member 300. It is contemplated that body 310 of engagement member 300 is substantially similar in size and configuration to head 12 of fastener 10 such that engagement member 300 can be loaded and advanced along end effector 200 similar to fastener 10.

In some embodiments, engagement member 300 may be brightly colored so that it is clearly visible through viewing window 204 of end effector 200. For example, in embodiments, engagement member 300 may be colored red, blue, green, yellow or the like.

With continued reference to FIGS. 4-6, engagement member 300 includes a biasing portion 316, having a pair of biasing arms 316a, 316b located within the respective radial gaps 314a, 314b of body 310. Biasing arms 316a, 316b are integrally formed with and extend from body 310 in a cantilevered fashion. In some embodiments, biasing arms 316a, 316b may be separable components that are attached to body 310 via, e.g., brazing, welding, an integrally formed living hinge or the like. Each biasing arm 316a, 316b terminates in a respective enlarged head portion 317a, 317b.

Biasing arms 316a, 316b may have an arcuate profile, as shown, and may lie substantially parallel to the proximal surface 310a of body 310. Biasing arms 316a, 316b may be disposed at a longitudinal position between the proximal surface 310a and the distal surface 310b of body 310. Biasing arms 316a, 316b are configured for pivotal movement with respect to the body 310. Biasing arms 316a, 316b have a flexible and/or resilient configuration, and accordingly may define a spring constant. Biasing arms 316a, 316b are biased toward a radially-outward or cantilevered configuration, as mentioned above. In this manner, biasing arms 316a, 316b are configured to pivot, flex or swing, radially outwardly with respect to body 310.

The movement of biasing arms 316a, 316b allows engagement member 300 to transition between a first configuration (FIG. 6), in which biasing arms 316a, 316b are approximated radially-inwardly toward body 310, and a second configuration (FIGS. 5A and 5B), in which biasing arms 316a, 316b are disposed radially outwardly with respect to body 310. With reference to FIG. 5B, biasing arms 316a, 316b may define a radius of curvature "R1", "R2" that approximates a radius of curvature "R3", "R4" defined by body 310 within the radial gaps 314a, 314b to accommodate folding the biasing arms 316a, 316b into the respective radial gaps 314a, 314b.

With reference to FIGS. 2A, 2B, and 4-5B, relative dimensions of end effector 200, engagement member 300, and fastener 10 will be detailed. For example, it is contemplated that a width "Y" of head portions 317a, 317b of biasing arms 316a, 316b is greater than a width "Z" of viewing windows 204 so that head portions 317a, 317b of biasing arms 316a, 316b do not lock out into viewing window 204 during actuation of end effector 200. Similarly, a thickness "W" of head portions 317a, 317b of biasing arms 316a, 316b is smaller than a width "X" of opposing lockout windows 210a, 210b such that the head portions 317a, 317b of biasing arms 316a, 316b can spring outward and grasp or enter into the opposing lockout windows 210a, 210b. However, the width "X" of opposing lockout windows 210a, 210b is smaller than a thickness "V" (FIG. 4) of opposing threaded portions 12a, 12b of fastener 10 so that the plurality of fasteners 10 do not get caught in the opposing lockout windows 210a, 210b.

With reference to FIGS. 1-8, in operation, end effector 200 is operatively connected to endoscopic assembly 130 such that inner tube 216 of end effector 200 is rotated due to an actuation of trigger 114. As inner tube 216 is rotated about the longitudinal axis "A-A," with respect to coil member 212, the pair of tines 224a, 224b of inner tube 216 transmit the rotation of the inner tube 216 to the plurality of fasteners 10 and to engagement member 300. As a result, the plurality of fasteners 10 and engagement member 300 advance distally.

In particular, because the opposing threaded portions 12a, 12b of fastener 10 are threadably engaged with the longitudinal spaces "S" defined by the coil member 212, rotation of the tines 224a and 224b of inner tube 216 urges the opposing threaded portions 12a, 12b to rotate within the coil member 212 about the longitudinal axis "A-A" (FIG. 1A). This in turn causes distal advancement of the plurality of fasteners 10 through outer tube 202 of end effector 200 along a helical path defined by coil member 212. As fastener 10 approaches the distal end of end effector 200, a tissue snaring section 14 and a distal tip 16 of fastener 10 protrude from outer tube 202. Further engagement and rotation by the tines 224a and 224b of inner tube 216 causes fastener 10 to penetrate and advance through, e.g., mesh "M" and into tissue "T."

Due to the similar configuration between head 12 of fastener 10 and engagement member 300, rotation of inner tube 216 to distally advance the plurality of fasteners 10 also distally advances engagement member 300. Accordingly, after one of the plurality of fasteners 10 penetrates and advances into tissue "T," engagement member 300 has been advanced distally to the next adjacent graduated cutout 204a, corresponding to the number of fasteners 10 still remaining within end effector 200.

It is contemplated that the location of the opposing lockout windows 210a, 210b on outer tube 202 is such that, upon firing the last fastener 10, engagement member 300 is distally advanced to, and aligned with, the opposing lockout windows 210a, 210b of outer tube 202. Because the thickness "W" of the head portions 317a, 317b of biasing arms 316a, 316b is smaller than the width "X" of each opposing lockout window 210a, 210b of outer tube 202, the axial and radial alignment between head portions 317a, 317b of biasing arms 316a, 316b of engagement member 300 and the opposing lockout windows 210a, 210b allows for the biasing arms 316a, 316b to spring radially outward and for head portions 317a, 317b to enter into a respective lockout window of opposing lockout windows 210a, 210b. At the same time, opposing threaded portions 312a, 312b of engagement member 300 remain engaged with inner tube 216. As a result of the engagement of head portions 317a, 317b of engagement member 300 in lockout windows 210a, 210b of outer tube 202, and the engagement of tines 224a and 224b of inner tube 216 against threaded portions 312a, 312b of engagement member 300, further rotation of inner tube 216 is mechanically prevented. Therefore, end effector 200 is prevented from further actuation. If additional fasteners 10 are required to complete the surgical procedure, spent end effector 200 may be replaced with a new end effector 200.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:

1. An end effector comprising:
   an outer tube defining a viewing window and a lockout window, the outer tube defining a first passageway therethrough;
   a coil member disposed within the first passageway of the outer tube, the coil member defining a second passageway therethrough;
   a plurality of fasteners disposed in the second passageway of the coil member, the plurality of fasteners configured to translate along the second passageway; and
   an engagement member disposed proximal to the plurality of fasteners and at least partially visible through the viewing window of the outer tube, the engagement member configured to translate along the second passageway proximal to the plurality of fasteners to provide a count relative to the viewing window of the plurality of fasteners remaining in the end effector, the engagement member including:
   a body portion; and
   a biasing portion extending from the body portion, the biasing portion having a biasing arm, the biasing arm biased resiliently outward such that engagement of a free end of the biasing portion of the engagement member with the lockout window restricts further translation of the engagement member, wherein the biasing arm of the engagement member includes a first biasing arm and a second biasing arm and wherein the outer tube includes a pair of lockout windows configured to engage with the first and second biasing arms of the engagement member.

2. The end effector according to claim 1, wherein the outer tube includes indicia disposed along the viewing window to indicate the count of the plurality of fasteners remaining in the end effector.

3. The end effector according to claim 1, further including an inner tube rotatably supported in the second passageway of the coil member, the inner tube defining a third passageway, the inner tube having:
   a first tine; and
   a second tine, wherein the first and second tines are radially opposed and define a first channel and a second channel therebetween.

4. The end effector according to claim 3, wherein the plurality of fasteners are disposed in the third passageway of the inner tube, the plurality of fasteners each including a pair of opposed threaded portions, the threaded portions of the plurality of fasteners being configured to extend radially beyond the first channel and the second channel of the inner tube respectively.

5. The end effector according to claim 4, wherein the threaded portions of the plurality of fasteners are configured to engage a plurality of successive winds of coil of the coil member.

6. The end effector according to claim 1, wherein the engagement member includes a body and a pair of a threaded portions protruding radially from the body thereof.

7. The end effector according to claim 6, wherein the first and second biasing arms are approximated radially-inward toward the body of the engagement member in a first configuration of the engagement member.

8. The end effector according to claim 6, wherein the first and second biasing arms are disposed radially-outward with respect to the body of the engagement member in a second configuration of the engagement member, when the free end of the biasing arm is in registration with the lockout window.

9. The end effector according to claim 1, wherein a width of a head portion of each of the first and second biasing arms is greater than a width of the viewing window such that the head portions of the first and second biasing arms do not engage the viewing window during actuation of the end effector.

10. The end effector according to claim 1, wherein a thickness of a head portion of each of the first and second biasing arms is smaller than a width of each lockout window such that the head portions of the first and second biasing arms engage respective lockout windows, when the head portions of the first and second biasing arms are in registration with the respective lockout windows.

11. The end effector according to claim 10, wherein when the head portions of the first and second biasing arms of the engagement member engage the respective lockout windows, and when the threaded portions of the body of the engagement member engage the inner tube, the inner tube is unable to rotate relative to the outer tube.

12. An end effector comprising:
an outer tube defining a viewing window and a lockout window, the outer tube defining a first passageway therethrough;
a coil member disposed within the first passageway of the outer tube, the coil member defining a second passageway therethrough;
an inner tube rotatably supported in the second passageway of the coil member, the inner tube defining a third passageway, the inner tube including:
a first tine; and
a second tine, wherein the first and second tines are radially opposed and define a first channel and a second channel therebetween;
a plurality of fasteners disposed within the third passageway of the inner tube, the plurality of fasteners configured to translate along the third passageway; and
an engagement member disposed proximal to the plurality of fasteners and visible through the viewing window of the outer tube, the engagement member configured to translate along the third passageway proximal to the plurality of fasteners to provide a count of the plurality of fasteners remaining in the third passageway, the engagement member including:
a body portion; and
a biasing portion extending from the body portion, the biasing portion having a first biasing arm and a second biasing arm, the first and second biasing arms biased resiliently outward such that engagement of a free end of the biasing portion of the engagement member with the lockout window restricts further translation of the engagement member.

13. The end effector according to claim 12, wherein the outer tube includes indicia disposed along the viewing window to indicate the count of the plurality of fasteners remaining in the end effector.

14. The end effector according to claim 12, wherein the plurality of fasteners each include pair of opposed threaded portions, the threaded portions of the plurality of fasteners being configured to extend radially beyond the first channel and the second channel of the inner tube respectively.

15. The end effector according to claim 14, wherein the outer tube includes a pair of opposing lockout windows configured to engage with the first and second biasing arms of the engagement member.

16. The end effector according to claim 15, wherein each of the first and second biasing arms includes a head portion.

17. The end effector according to claim 16, wherein when the head portions of the first and second biasing arms of the engagement member engage the respective lockout windows, and when the threaded portions of the body of the engagement member engage the inner tube, the inner tube is unable to rotate relative to the outer tube.

18. The end effector according to claim 15, wherein the opposing lockout windows are located on the outer tube such that when a last fastener of the plurality of fasteners is fired, the first and second biasing arms of the engagement member are in registration with the respective lockout windows.

19. An end effector comprising:
an outer tube defining a viewing window and a pair of lockout windows, the outer tube defining a first passageway therethrough;
a coil member disposed within the first passageway of the outer tube, the coil member defining a second passageway therethrough;
a plurality of fasteners disposed in the second passageway of the coil member, the plurality of fasteners configured to translate along the second passageway; and
an engagement member disposed proximal to the plurality of fasteners and at least partially visible through the viewing window of the outer tube, the engagement member configured to translate along the second passageway proximal to the plurality of fasteners to provide a count relative to the viewing window of the plurality of fasteners remaining in the end effector, the engagement member including:
a body portion; and
a first biasing arm and a second biasing arm each extending from the body portion, each biasing arm biased resiliently outward, wherein the pair of lockout windows is configured to engage with the first and second biasing arms of the engagement member, and engagement of a free end of each biasing arm with a respective lockout window of the pair of lockout windows restricts further translation of the engagement member.

* * * * *